(12) United States Patent
Gatchell et al.

(10) Patent No.: US 8,409,336 B2
(45) Date of Patent: Apr. 2, 2013

(54) AIR FILTER SYSTEM

(75) Inventors: Stephen M. Gatchell, Cordova, TN (US); Benjamin David Freeman, Bartlett, TN (US)

(73) Assignee: Hunter Fan Company, Memphis, TN (US)

( * ) Notice: Subject to any disclaimer, the term of this patent is extended or adjusted under 35 U.S.C. 154(b) by 218 days.

(21) Appl. No.: 12/855,900

(22) Filed: Aug. 13, 2010

(65) Prior Publication Data

US 2011/0048238 A1   Mar. 3, 2011

Related U.S. Application Data

(60) Provisional application No. 61/238,776, filed on Sep. 1, 2009.

(51) Int. Cl.
*B03C 3/155* (2006.01)

(52) U.S. Cl. .................. 96/67; 55/497; 55/521; 55/524; 96/69

(58) Field of Classification Search ................ 96/67, 69; 55/497, 521, 524, DIG. 31
See application file for complete search history.

(56) References Cited

U.S. PATENT DOCUMENTS

| | | | | |
|---|---|---|---|---|
| 2,814,355 A * | 11/1957 | Powers | ............................. | 96/67 |
| 3,181,284 A * | 5/1965 | Copenhefer | ....................... | 96/67 |
| 3,237,382 A * | 3/1966 | Berly | ................................. | 96/67 |
| 3,997,304 A * | 12/1976 | Carr | ................................... | 96/67 |
| 4,509,958 A * | 4/1985 | Masuda et al. | ..................... | 96/60 |
| 4,715,870 A * | 12/1987 | Masuda et al. | ..................... | 96/67 |
| 4,978,372 A * | 12/1990 | Pick | ................................... | 96/67 |
| 5,540,761 A * | 7/1996 | Yamamoto | ....................... | 96/67 |
| 6,497,754 B2 * | 12/2002 | Joannou | ........................... | 96/67 |
| 6,579,350 B2 * | 6/2003 | Doherty | ........................... | 96/67 |
| 6,635,106 B2 * | 10/2003 | Katou et al. | ..................... | 96/67 |
| 7,691,186 B2 * | 4/2010 | Wiser | ............................... | 96/17 |
| 2005/0172812 A1 * | 8/2005 | Ueda et al. | ........................ | 96/67 |

FOREIGN PATENT DOCUMENTS

JP             60-172362 A  *  9/1985  ........................ 96/67

* cited by examiner

*Primary Examiner* — Richard L Chiesa
(74) *Attorney, Agent, or Firm* — Baker Donelson; Dorian B. Kennedy

(57) ABSTRACT

An air filter system (10) has a filter housing (11), an air filter media (12), and an electrical circuit (13) electrically coupled to the media. The filter media consists of a pleated air filter material (23) with front pleat apexes (25) and rear pleat apexes (26) which are coated with an electrically conductive material to form front vertical strips (27) and rear strips (28). The electrical circuit includes a positive front electrical contact (30) and a rear electrical contact (31). The front electrical contact has a rear surface (30') in electrical contact with an elongated front electrical contact bar (33), oriented horizontally across and in electrical contact with the filter front strips of conductive ink. Similarly, the rear electrical contact has a front surface (31') in electrical contact with an elongated rear electrical contact bar (34), oriented horizontally across and in electrical contact with the rear strips of conductive ink.

17 Claims, 5 Drawing Sheets

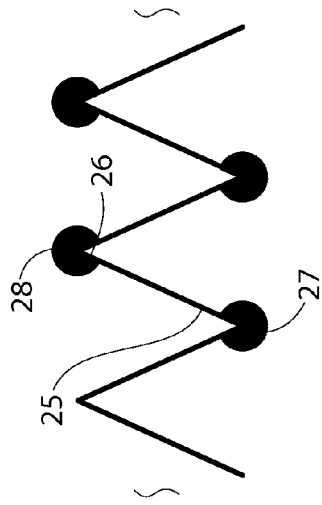
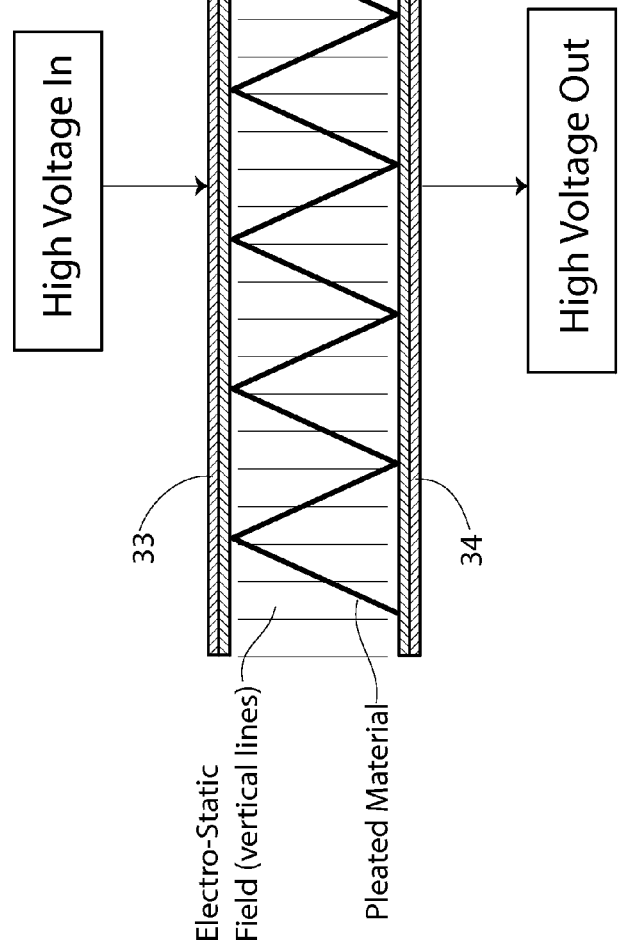

AIR FILTER SYSTEM

REFERENCE TO RELATED APPLICATION

Applicant claims the benefit of U.S. Provisional Patent Application Ser. No. 61/238,776 filed Sep. 1, 2009.

TECHNICAL FIELD

This invention relates to air filters that operate independently or in conjunction with a heating, ventilation and air conditioning system.

BACKGROUND OF THE INVENTION

The air return of most heating, ventilation and air conditioning (HVAC) systems is provided with an air filter to remove airborne dust and other airborne contaminants that could clog and/or cover the coils of the evaporator or heating element of the HVAC system. These filters also trap microorganisms that may cause illnesses.

Air filters or purifiers also exists which work independently or as a stand alone unit to remove contaminants from the air. The units also utilize a filter media to capture the contaminants, including microorganisms.

Accordingly, it is seen that a need exists for a filter system which may inhibit the growth of microorganisms within an environment. It thus is to the provision of such that the present invention is primarily directed.

SUMMARY OF THE INVENTION

An air filter system comprises a multi-pleated air filter medium forming a plurality of elongated front fold apexes and a plurality of elongated rear fold apexes, a first conductive coating applied to the plurality of elongated front fold apexes to form a plurality of elongated conductive front strips, a second conductive coating applied to the plurality of elongated rear fold apexes to form a plurality of elongated conductive rear strips, an elongated front contact bar extending across and in electrical contact with the plurality of elongated conductive front strips, an elongated rear contact bar extending across and in electrical contact with the plurality of elongated conductive rear strips, and a frame mounted about the periphery of the multi-pleated air filter medium. With this construction, an electric source may be coupled to the front contact bar and rear contact bar to create a voltage fielded and a current flowing through the filter media to inhibit the growth and sterilize microorganisms that become trapped in the filter media.

BRIEF DESCRIPTION OF THE DRAWINGS

FIG. 6 is a schematic view of a portion of the filter system of FIG. 1, showing the produced electro-static field.

FIG. 7 is an enlarged schematic view of a portion of the filter of FIG. 1.

DETAILED DESCRIPTION

Figure 1:
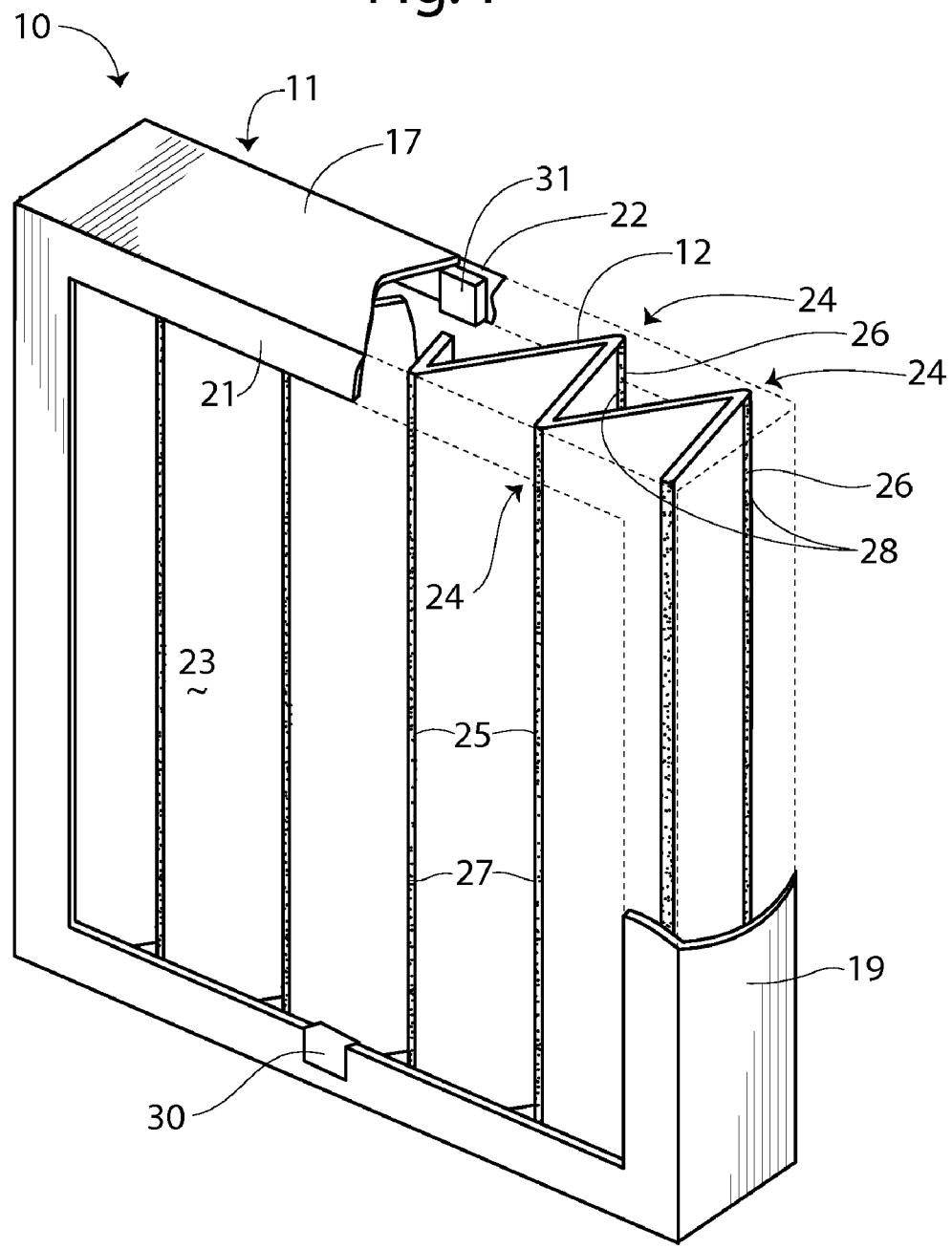
FIG. 1 is a perspective view of the air filter system in a preferred form of the invention, shown with a portion removed for clarity of explanation.
Figure 2:
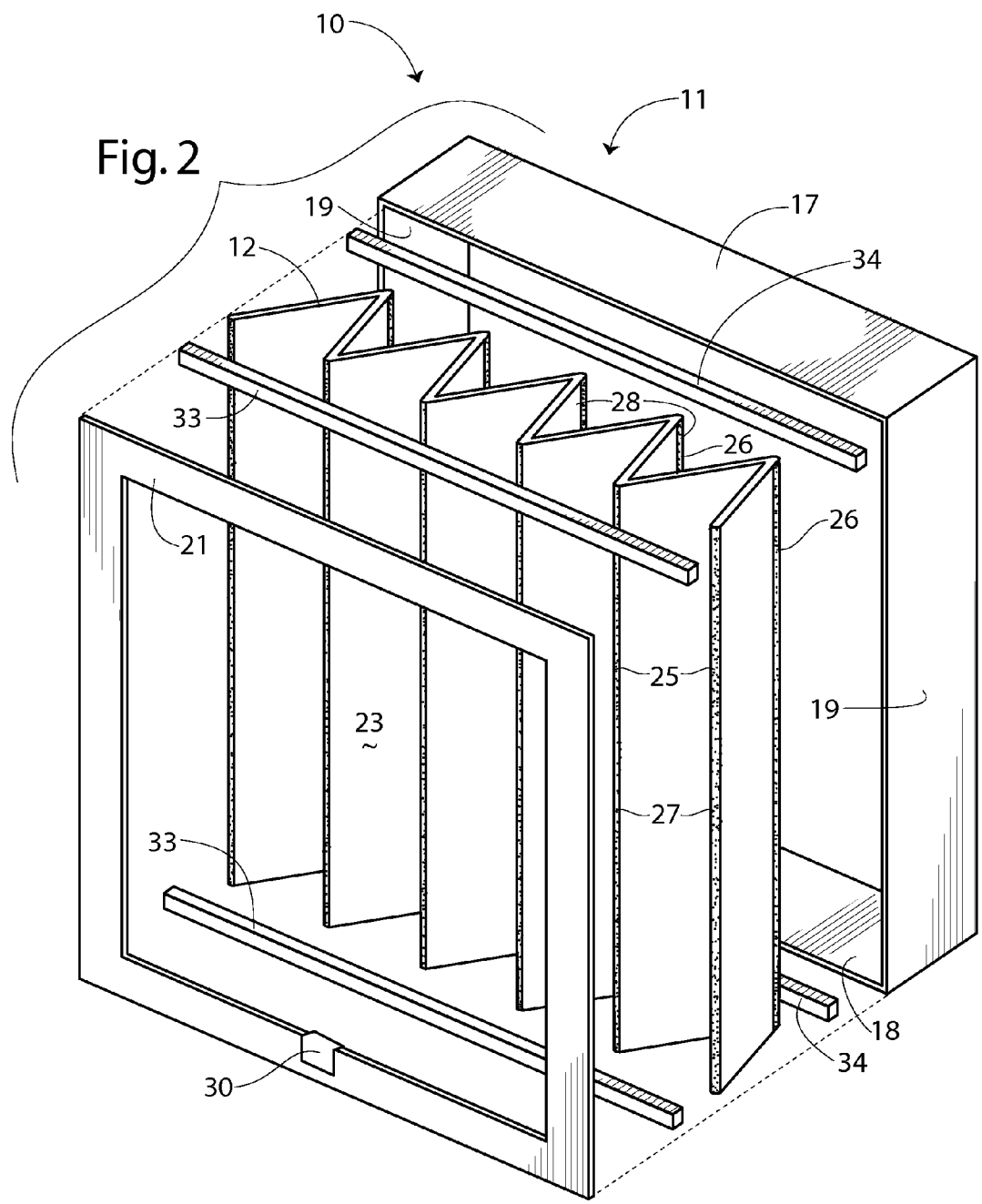
FIG. 2 is an exploded view of a portion of the filter system of FIG. 1.
Figure 3:
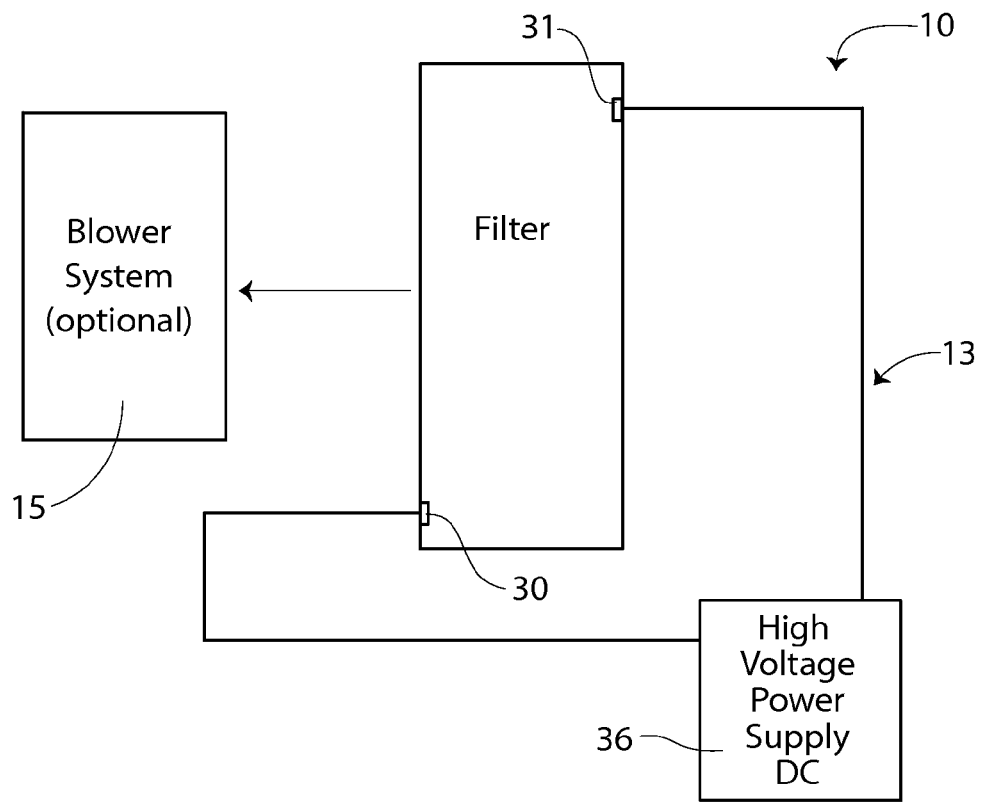
FIG. 3 is a schematic view of the air filter system of FIG. 1 shown schematically coupled to auxiliary equipment.
Figure 4:
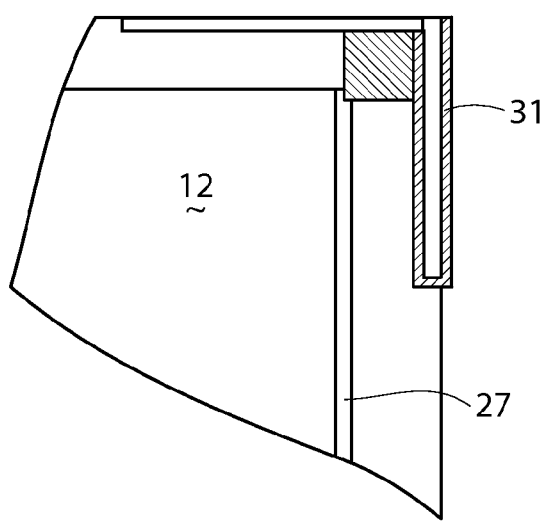
FIG. 4 is an enlarged view of a portion of the filter system of FIG. 1.

With reference next to the drawings, there is shown an air filter system 10 in a preferred form of the invention. The air filter system 10 includes a filter housing 11, an air filter media 12, and an accompanying electrical circuit 13 electrically coupled to the media 12. The air filter system 10 may or may not include an air blower 15, depending upon the use of the filter system as a stand alone system or in conjunction with an additional HVAC system.

The housing 11 has a rectangular frame or arrangement of support walls which include a top wall 17, bottom wall 18, and two oppositely disposed side walls 19. The frame also includes an inside front flange 21 and inside rear flange 22 extending inwardly from the support walls.

The filter media 12 consists of a sheet of air filter material 23, such as a polypropylene melt-blow material made by Shuenn Bao Shing Corporation of Chang Hwa Hsien, Taiwan which is considered to filter air particles of a size greater than or equal to 0.1 micron and a 99.7% effectiveness. The filter material 23 is folded to form a series of vertically oriented pleats 24, however the orientation of the multi-pleats is not important. The front side of the media has a horizontal array of vertical front pleat apexes 25, while the rear side of the media has a horizontal array of vertical rear pleat apexes 26. The term front and rear as used herein is intended to represent the orientation of the filter relative to the flow of air therethrough with the front being oriented upstream of the rear. The filter media 12 may include a conventional comb and stabilizer to maintain the formation of the pleats.

As part of the electrical circuit 13, the front and rear pleat apexes 25 and 26 are treated or coated with an electrically conductive ink, paint or other material, such as a carbon based ink, that binds to the air filter material 23 to form front vertical lines or strips 27 and rear vertical lines or strips 28 of conductive material along each respective apex 25 and 26.

The electrical circuit 13 also includes a positive front electrical contact or contact member 30 and a negative rear electrical contact or contact member 31, each of which may be made of a conductive foil such as aluminum foil made by Kunshan Hanpin Dianzi Co., Ltd. The front electrical contact 30 has a rear surface 30' in electrical contact with an elongated front electrical contact bar 33 oriented horizontally across and in electrical contact with the filter front vertical lines 27 of conductive ink. Similarly, the rear electrical contact 31 has a front surface 31' in electrical contact with an elongated rear electrical contact bar 34, oriented horizontally across and in electrical contact with the filter rear vertical lines 28 of conductive ink. The front and rear electrical contact bars 33 and 34 may be made of a pliable, conductive carbon foam or felt, such as the conductive foam made by Chao-Yang Electric Mfg., Co., LTD, of Yung Kang City, Tainan Hsien, Taiwan. The front electrical contact 30 is electrically coupled to a high voltage d.c. power supply 36 while the rear electrical contact 31 is coupled to ground so that the current passes from front contact 30 to rear contact 31. To enable quick and easy connection with the voltage supply 36, the front electrical contact 30 has an exposed front surface 30" and the rear electrical contact 31 has an exposed rear surface 31". As such, the filter may be mounted in place with the contacts 30 and 31 positioned for immediate contact with exposed matching electrical contacts coupled to the power supply and mounted upon the auxiliary equipment associated with the filter device. To insure proper contact between the contacts 30 and 31 and the auxiliary electrical contacts, the front contact front surface 30' preferably protrudes forwardly of the front surface of the front flange 21. Similarly, it is preferred that the rear contact rear surface 30' protrude rearwardly of the rear surface of the rear flange 22.

Figure 5:
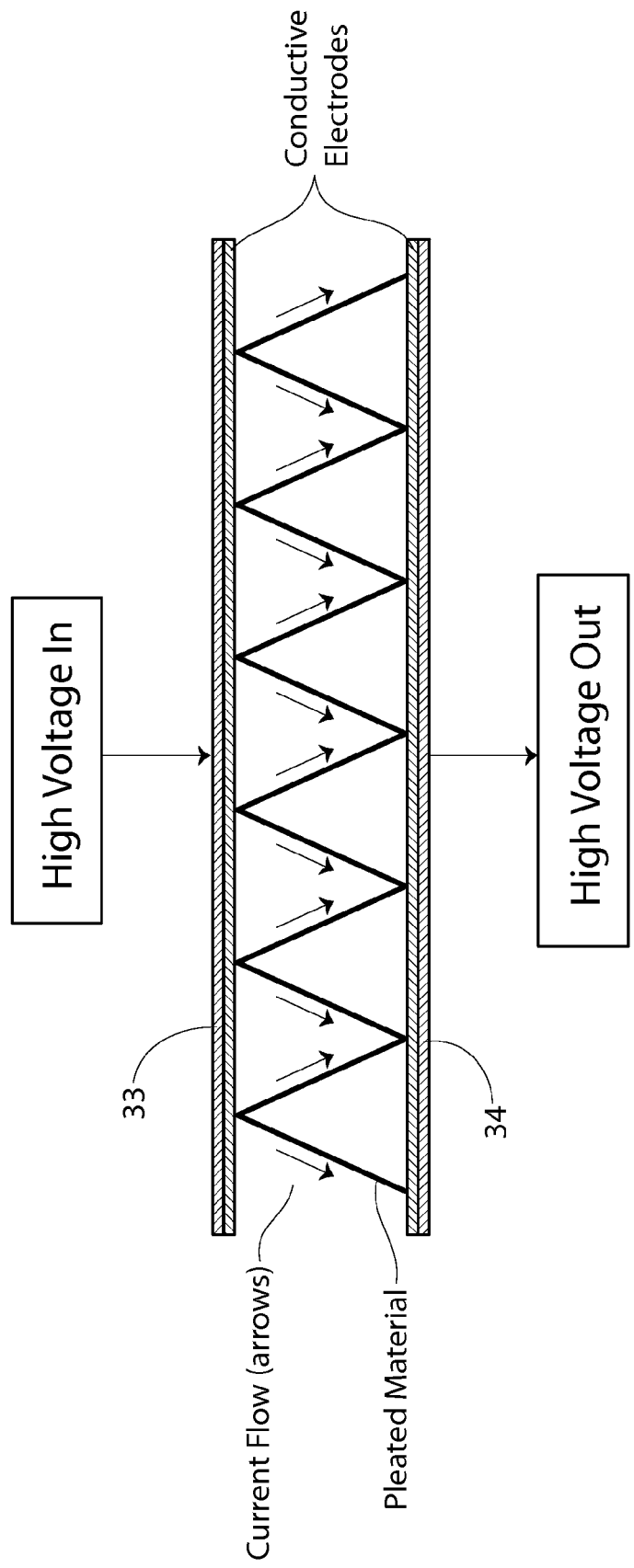
FIG. 5 is a schematic view of a portion of the filter system of FIG. 1, showing the current passing through the filter media.

In use, the d.c. power supply 36 preferably provides a voltage range of 2 Kilovolts to 17 Kilovolts (preferably 12 Kilovolts) of d.c. power with a current range of 1 to 50 micro amperes (preferably 40 micro amperes). The positive current is applied to the front contact 30 while the negative current is applied to the rear contact 31. This current is passed to the front contact 30 and rear contact 31 which in turn passes the current to the front and rear electrical strips 33 and 34. The current is then passed to the filter front and rear vertical lines 27 and 28 of the filter media pleats. The current flow passes through the filter media as depicted by the arrows in FIG. 5. This electric current through the filter media creates an electro-static field, which is represented by the vertical lines in FIG. 6.

The high voltage field and a certain amount of current flowing through the filter media provides an environment that inhibits the growth and sterilizes microorganisms that become trapped in the filter media as contaminated air is passed through the filter.

It thus is seen that an air filter system is now provided that inhibits the growth of microorganisms. It should be understood that many modifications may be made to the specific preferred embodiment described herein, in addition to those specifically recited, without departure from the spirit and scope of the invention as described by the following claims.

The invention claimed is:

1. An air filter system comprising,
a multi-pleated air filter media forming a plurality of elongated front fold apexes and a plurality of elongated rear fold apexes, said air filter media being electrically conductive;
a first conductive coating applied to said plurality of elongated front fold apexes to form a plurality of elongated conductive front strips;
a second conductive coating applied to said plurality of elongated rear fold apexes to form a plurality of elongated conductive rear strips;
an elongated front contact bar extending across and in electrical contact with said plurality of elongated conductive front strips;
an elongated rear contact bar extending across and in electrical contact with said plurality of elongated conductive rear strips, and
a frame mounted about the periphery of said multi-pleated air filter media,
whereby an electric source may be coupled to the front contact bar and rear contact bar to create a voltage field and a current flowing through the filter media to inhibit the growth and sterilize microorganisms that become trapped in the filter media.

2. The air filter system of claim 1 wherein said filter media is made of a polypropylene material.

3. The air filter system of claim 1 further comprising a second elongated front contact bar extending across and in electrical contact with said plurality of elongated conductive front strips, and a second elongated rear contact bar extending across and in electrical contact with said plurality of elongated conductive rear strips.

4. The air filter system of claim 1 further comprising a front electrical contact member mounted to said frame and in electrical contact with said front contact bar.

5. The air filter system of claim 4 further comprising a rear electrical contact member mounted to said frame and in electrical contact with said rear contact bar.

6. The air filter system of claim 1 wherein said front contact bar is made of a pliable material.

7. The air filter system of claim 6 wherein said front contact bar pliable material is a conductive carbon foam or felt.

8. The air filter system of claim 6 wherein said rear contact bar is made of a pliable material.

9. The air filter system of claim 8 wherein said front contact bar pliable material and said rear contact bar pliable material is a conductive carbon foam or felt.

10. The air filter system of claim 1 wherein said frame includes peripheral walls, an inwardly facing front flange extending from said peripheral walls, and an inwardly facing rear flange extending from said peripheral walls, and wherein said front electrical contact member has a forward surface to make electrical contact forwardly of said frame and a rearward surface to make electrical contact with said front contact bar rearward of said frame, and wherein said rear electrical contact member has a rearward surface to make electrical contact rearwardly of said frame and a forward surface to make electrical contact with said rear contact bar forward of said frame.

11. An air filter system comprising,
a multi-pleated air filter media forming a plurality of elongated front fold apexes and a plurality of elongated rear fold apexes, said air filter media being electrically conductive;
a conductive coating applied to said plurality of elongated front fold apexes to form a plurality of elongated conductive front strips and applied to said plurality of elongated rear fold apexes to form a plurality of elongated conductive rear strips;
an elongated front contact bar extending across and in electrical contact with said plurality of elongated conductive front strips;
an elongated rear contact bar extending across and in electrical contact with said plurality of elongated conductive rear strips, and
a frame mounted about the periphery of said multi-pleated air filter media, said frame having peripheral support walls, a front flange extending from at least one said peripheral support walls, and a rear flange extending from at least one said peripheral walls, a front contact mounted to said front flange and having a forward surface to make electrical contact forwardly of said frame and a rearward surface to make electrical contact with said front contact bar rearward of said frame, and a rear contact mounted to said rear flange and having a rearward surface to make electrical contact rearwardly of said frame and a forward surface to make electrical contact with said rear contact bar forward of said frame,
whereby an electric source may be coupled to the front contact bar and rear contact bar to create a voltage field and a current flowing through the filter media to inhibit the growth and sterilize microorganisms that become trapped in the filter media.

12. The air filter system of claim 11 wherein said filter media is made of a polypropylene material.

13. The air filter system of claim 11 further comprising a second elongated front contact bar extending across and in electrical contact with said plurality of elongated conductive front strips, and a second elongated rear contact bar extending across and in electrical contact with said plurality of elongated conductive rear strips.

14. The air filter system of claim 11 wherein said front contact bar is made of a pliable material.

15. The air filter system of claim 14 wherein said front contact bar pliable material is a conductive carbon foam or felt.

16. The air filter system of claim 14 wherein said rear contact bar is made of a pliable material.

17. The air titter system of claim 16 wherein said front contact bar pliable material and said rear contact bar pliable material is a conductive carbon foam or felt.

* * * * *